US012076167B2

(12) United States Patent
Al Hatib et al.

(10) Patent No.: US 12,076,167 B2
(45) Date of Patent: Sep. 3, 2024

(54) PREDICTIVE WEIGHTING OF HYPOTENSION PROFILING PARAMETERS

(71) Applicant: Edwards Lifesciences Corporation, Irvine, CA (US)

(72) Inventors: Feras Al Hatib, Irvine, CA (US); Zhongping Jian, Irvine, CA (US); Sai Prasad Buddi, Costa Mesa, CA (US)

(73) Assignee: EDWARDS LIFESCIENCES CORPORATION, Irvine, CA (US)

( * ) Notice: Subject to any disclaimer, the term of this patent is extended or adjusted under 35 U.S.C. 154(b) by 1003 days.

(21) Appl. No.: 16/927,233

(22) Filed: Jul. 13, 2020

(65) Prior Publication Data
US 2020/0337649 A1 Oct. 29, 2020

Related U.S. Application Data

(63) Continuation of application No. 15/634,918, filed on Jun. 27, 2017, now Pat. No. 10,751,004.
(Continued)

(51) Int. Cl.
*A61B 5/021* (2006.01)
*A61B 5/00* (2006.01)
(Continued)

(52) U.S. Cl.
CPC ........ *A61B 5/7275* (2013.01); *A61B 5/02028* (2013.01); *A61B 5/021* (2013.01);
(Continued)

(58) Field of Classification Search
CPC ... A61B 5/7275; A61B 5/02028; A61B 5/021; A61B 5/7239; A61B 5/746; A61B 5/02042; G16H 50/30
(Continued)

(56) References Cited

U.S. PATENT DOCUMENTS 5,482,036 A 1/1996 Diab et al.
5,819,226 A 10/1998 Gopinathan et al.
(Continued)

FOREIGN PATENT DOCUMENTS

EP 2679256 A1 1/2014
EP 2730302 A1 5/2014
(Continued)

OTHER PUBLICATIONS

Chen, X. et al., Forecasting Acute Hypotensive Episodes in Intensive Care Patients Based on a Peripheral Arterial Blood Pressure Waveform, Computers in Cardiology 2009; 36:545-548.
(Continued)

*Primary Examiner* — Navin Natnithithadha
(74) *Attorney, Agent, or Firm* — David R. Fairbairn; KINNEY & LANGE, P.A.

(57) ABSTRACT

A system having a processor obtain a digital hemodynamic data from a hemodynamic sensor, obtain one or more vital sign parameters characterizing vital sign data from the digital hemodynamic data, derive differential parameters based on the one or more vital sign parameters, generate combinatorial parameters using the one or more vital sign parameters and the differential parameters, determine a risk score corresponding to a probability of a future hypotension event for the living subject based on a weighted combination of a plurality of hypotension profiling parameters including the one or more vital sign parameters characterizing vital sign data, the differential parameters and the combinatorial parameters, and invoke a sensory alarm if the risk score satisfies a predetermined risk criterion.

26 Claims, 5 Drawing Sheets

Related U.S. Application Data

(60) Provisional application No. 62/360,088, filed on Jul. 8, 2016.

(51) Int. Cl.
*A61B 5/02* (2006.01)
*G16H 50/30* (2018.01)

(52) U.S. Cl.
CPC ............ *A61B 5/7239* (2013.01); *A61B 5/746* (2013.01); *G16H 50/30* (2018.01); *A61B 5/02042* (2013.01)

(58) Field of Classification Search
USPC .......................... 600/481, 483–485, 486, 488
See application file for complete search history.

(56) References Cited

U.S. PATENT DOCUMENTS

| | | |
|---|---|---|
| 7,572,230 B2 | 8/2009 | Neumann et al. |
| 8,478,389 B1 | 7/2013 | Brockway et al. |
| 9,662,028 B2 | 5/2017 | Vainoras et al. |
| 2003/0036685 A1 | 2/2003 | Goodman |
| 2003/0149453 A1 | 8/2003 | Kroll et al. |
| 2003/0167010 A1 | 9/2003 | Pinsky |
| 2005/0187796 A1 | 8/2005 | Rosenfeld et al. |
| 2008/0200775 A1* | 8/2008 | Lynn ...................... A61B 5/366 128/200.24 |
| 2008/0319332 A1 | 12/2008 | Sommo et al. |
| 2011/0245631 A1 | 10/2011 | Genc |
| 2012/0271612 A1 | 10/2012 | Barsoum et al. |
| 2013/0023776 A1 | 1/2013 | Olde et al. |
| 2013/0096402 A1 | 4/2013 | Olde et al. |
| 2013/0204542 A1 | 8/2013 | Olde et al. |
| 2013/0262357 A1 | 10/2013 | Amarasingham et al. |
| 2014/0107433 A1 | 4/2014 | Wegerich |
| 2014/0107504 A1 | 4/2014 | Stapelfeldt et al. |
| 2014/0279754 A1 | 9/2014 | Barsoum et al. |
| 2014/0323885 A1 | 10/2014 | Genc et al. |
| 2014/0364750 A1 | 12/2014 | Brumfield et al. |
| 2015/0025329 A1 | 1/2015 | Amarasingham et al. |
| 2015/0065826 A1 | 3/2015 | Mulligan et al. |
| 2015/0116333 A1 | 4/2015 | Harper et al. |
| 2015/0150514 A1 | 6/2015 | Batchinsky et al. |
| 2015/0164437 A1 | 6/2015 | McCombie et al. |
| 2015/0282717 A1 | 10/2015 | McCombie et al. |
| 2015/0297143 A1 | 10/2015 | Rajan et al. |
| 2015/0347698 A1 | 12/2015 | Soni et al. |
| 2016/0012197 A1 | 1/2016 | Eromo et al. |
| 2016/0142894 A1 | 5/2016 | Papakonstantinou et al. |
| 2016/0143596 A1 | 5/2016 | Bhattacharya et al. |
| 2016/0378943 A1 | 12/2016 | Vallée |
| 2017/0076211 A1 | 3/2017 | Kusumura et al. |
| 2017/0116497 A1 | 4/2017 | Georgescu et al. |
| 2017/0235917 A1 | 8/2017 | Bighamian et al. |
| 2017/0308981 A1 | 10/2017 | Razavian et al. |
| 2018/0008205 A1 | 1/2018 | Al Hatib et al. |
| 2018/0020989 A1 | 1/2018 | Al Hatib et al. |
| 2018/0025290 A1 | 1/2018 | Al Hatib et al. |
| 2018/0028076 A1 | 2/2018 | Al Hatib et al. |
| 2018/0182492 A1 | 6/2018 | Yamashita |
| 2018/0322951 A1 | 11/2018 | Vairavan et al. |
| 2019/0307337 A1 | 10/2019 | Little et al. |
| 2020/0260965 A1 | 8/2020 | Munoz et al. |
| 2021/0259629 A1 | 8/2021 | Smith et al. |
| 2022/0395236 A1 | 12/2022 | Buddi et al. |
| 2022/0400965 A1 | 12/2022 | Schneider et al. |
| 2023/0380697 A1 | 11/2023 | Buddi et al. |

FOREIGN PATENT DOCUMENTS

| | | | |
|---|---|---|---|
| KR | 10-2009-0049709 A | | 5/2009 |
| WO | 0241771 A1 | | 5/2002 |
| WO | 2004034898 A2 | | 4/2004 |
| WO | 2015183689 A1 | | 12/2015 |
| WO | 2016022989 A2 | | 2/2016 |

OTHER PUBLICATIONS

Chiarugi, F., Predicting the Occurrence of Acute Hypotensive Episodes: The PhysioNet Challenge; Computers in Cardiology 2009; 36:621-624.

Fournier, Pa, et al., Acute Hypotension Episode Prediction Using Information Divergence for a Feature Selection, and Non-Parametric Methods for Classification; Computers in Cardiology 2009; 36:625-628.

Hayn, D., A Biosignal Analysis Applied for Developing an Algorithm Predicting Critical Situations of High Risk Cardiac Patients by Hemodynamic Monitoring; Computers in Cardiology 2009; 36: 629-632.

Henriques, JH et al., Prediction of Acute Hypotensive Episodes Using Neural Network Multi-models; Computers in Cardiology 2009; 36-549-552.

Ho, Tct et al., Utilizing Histogram to Identify Patients Using Pressors for Acute Hypotension, Computers in Cardiology 2009; 36:797-800.

Jousset, F., Computers in Cardiology/Physionet Challenge 2009: Predicting Acute Hypotensive Episodes, 2009; 36:637-640.

Jin, K. et al., Smooting and Discriminating MAP Data; Computers in Cardiology 2009; 36: 633-636.

Langley, P., et al., Predicting Acute Hypotensive Episodes From Mean Arterial Pressure; Computers in Cardiology 2009; 36: 553-556.

Moody, GB et al.; Predicting Acute Hypotensive Episodes: The 10th Annual PhysioNet/Computers in Cardiology Challenge, 2009; 36:541-544.

Mneimneh, Ma, et al., A Rule-Based Approach for the Prediction of Acute Hypotensive Episodes; Computers in Cardiology 2009; 36:557-560.

Hastie, Trevor, Robert Tibshirani, and Jerome Friedman. The elements of statistical learning: data mining, inference, and prediction. Chapters 3 and 11. Springer Science & Business Media, 2009. (Year: 2009).

Hatib F, Jian Z, Buddi S, Lee C, Settels J, Sibert K, Rinehart J, Cannesson M. Machine-learning Algorithm to Predict Hypotension Based on High-fidelity Arterial Pressure Waveform Analysis. Anesthesiology. Oct. 2018; 129(4): 663-674.

Janghorbani et al., "Prediction of Acute Hypotension Episodes Using Logistic Regression Model and Support Vector Machine: A Comparative Study", IEEE, 19th Iranian Conference on Electrical Engineering (Year: 2011).

Liu et al., "Utility of Vital Signs, Heart Rate Variability and Complexity, and Machine Learning for Identifying the Need for Lifesaving Interventions in Trauma Patients," Shock, vol. 42, No. 2, pp. 108-114, 2014 (Year: 2014).

Maldonado, Sebastian, and Richard Weber. "A wrapper method for feature selection using support vector machines." Information Sciences 179, 13 (2009): 2208-2217. (Year: 2009).

Malik, Marek, et al. "Heart rate variability: Standards of measurement, physiological interpretation, and clinical use." European heart journal 17.3 (1996): 354-381. (Year: 1996).

Pinsky, M. R., "Protocolized Cardiovascular Management Based on Ventricular-arterial Coupling," Functional Hemodynamic Monitoring pp. 381-395, Jan. 2005.

Sannino, Giovanna, et al. "To what extent is it possible to predict fails due to standing hypotension by using HRV and wearable devices? Study design and preliminary results from a proof-of-concept study." International Workshop on Ambient Assisted Living. Springer, Cham, 2014. (Year: 2014).

\* cited by examiner

PREDICTIVE WEIGHTING OF HYPOTENSION PROFILING PARAMETERS

CROSS REFERENCE TO RELATED APPLICATIONS

This application is a continuation of U.S. patent application Ser. No. 15/634,918, filed Jun. 27, 2017, which claims priority to U.S. Provisional Application No. 62/360,088, filed Jul. 8, 2016, the entire contents of which are herein incorporated by reference in their entireties.

BACKGROUND

Hypotension, or low blood pressure, can be a harbinger of serious medical complications, and even mortality, for patients undergoing surgery and those acutely or critically ill patients receiving treatment in an intensive care unit (ICU). The dangers associated with the occurrence of hypotension in a patient are due both to the potential injury caused by the hypotension itself and to the many serious underlying medical disorders that the occurrence of hypotension may signify.

In and of itself, hypotension in surgical patients or critically ill patients is a serious medical condition. For example, in the operating room (OR) setting, hypotension during surgery is associated with increased mortality and organ injury. Even short durations of extreme hypotension during surgery are associated with acute kidney injury and myocardial injury. Among critically ill patients, in-hospital mortality may be nearly doubled for patients experiencing hypotension after emergency intubation. For surgical patients and seriously ill patients alike, hypotension, if not corrected, can impair organ perfusion, resulting in irreversible ischemic damage, neurological deficit, cardiomyopathy, and renal impairment.

In addition to posing serious risks to surgical patients and critically ill patients in its own right, hypotension can be a symptom of one or more other serious underlying medical conditions. Examples of underlying conditions for which hypotension may serve as an acute symptom include sepsis, myocardial infarction, cardiac arrhythmia, pulmonary embolism, hemorrhage, dehydration, anaphylaxis, acute reaction to medication, hypovolemia, insufficient cardiac output, and vasodilatory shock. Due to its association with such a variety of serious medical conditions, hypotension is relatively common, and is often seen as one of the first signs of patient deterioration in the OR and ICU. For instance, hypotension is seen in up to approximately thirty-three percent of surgeries overall, and up to eighty-five percent in high risk surgeries. Among ICU patients, hypotension occurs in from approximately twenty-four percent to approximately eighty-five percent of all patients, with the eighty-five percent occurrence being seen among critically ill patients.

Conventional patient monitoring for hypotension in the OR and ICU settings can include continuous or periodic blood pressure measurement. However, such monitoring, whether continuous or periodic, typically provides no more than a real-time assessment. As a result, hypotension in a surgical patient or critically ill patient is usually detected only after it begins to occur, so that remedial measures and interventions cannot be initiated until the patient has entered a hypotensive state. Although, as noted above, extreme hypotension can have potentially devastating medical consequences quite quickly, even relatively mild levels of hypotension can herald or precipitate cardiac arrest in patients with limited cardiac reserve.

In view of the frequency with which hypotension is observed to occur in the OR and ICU settings, and due to the serious and sometimes immediate medical consequences that can result when it does occur, a solution enabling prediction of a future hypotension event, before its occurrence, is highly desirable.

SUMMARY

There are provided systems and methods for performing predictive weighting of hypotension profiling parameters, substantially as shown in and/or described in connection with at least one of the figures, and as set forth more completely in the claims.

DETAILED DESCRIPTION

Figure 1:
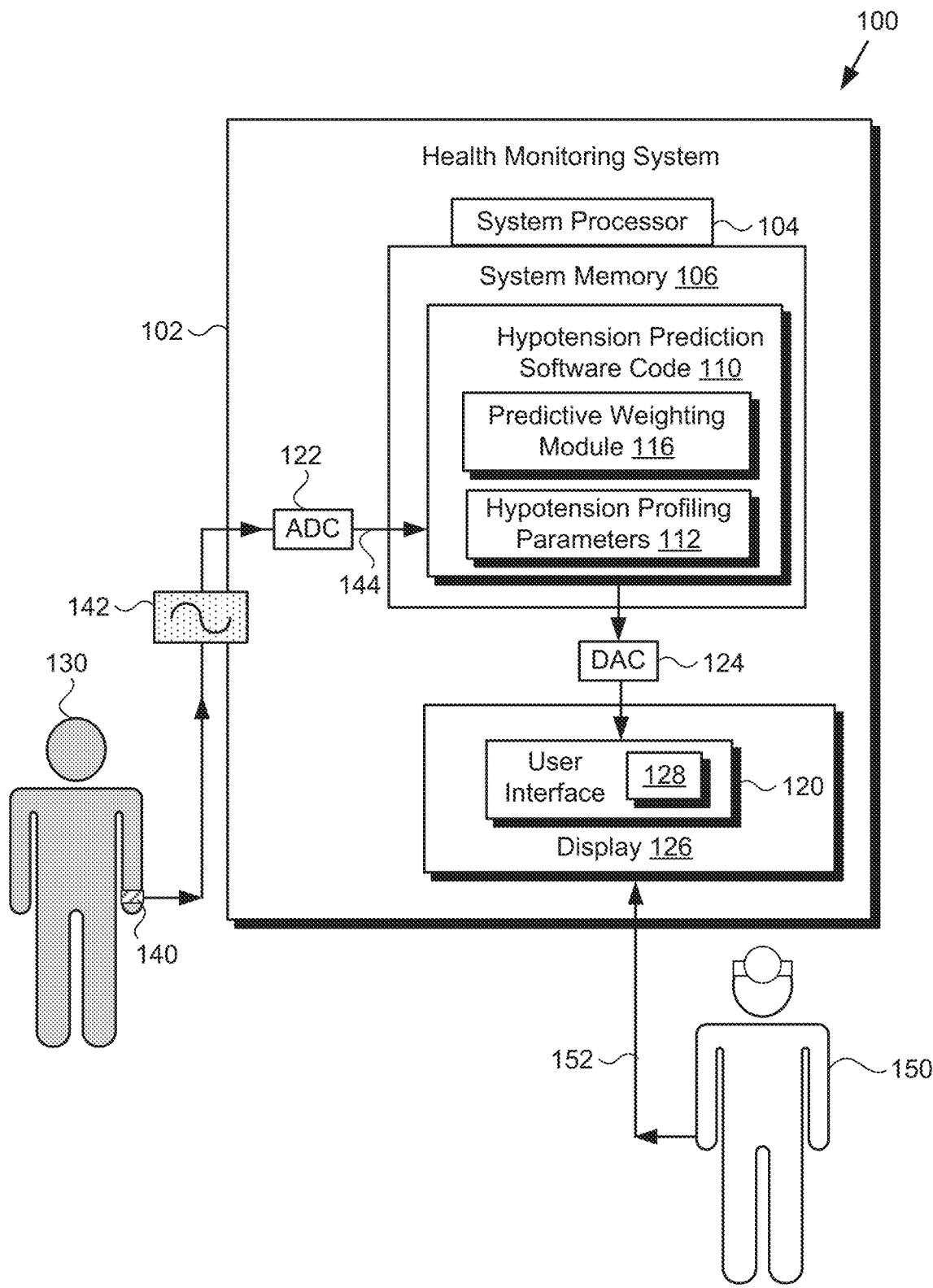
FIG. 1 shows a diagram of an exemplary system for performing predictive weighting of hypotension profiling parameters, according to one implementation.

The following description contains specific information pertaining to implementations in the present disclosure. One skilled in the art will recognize that the present disclosure may be implemented in a manner different from that specifically discussed herein. The drawings in the present application and their accompanying detailed description are directed to merely exemplary implementations. Unless noted otherwise, like or corresponding elements among the figures may be indicated by like or corresponding reference numerals. Moreover, the drawings and illustrations in the present application are generally not to scale, and are not intended to correspond to actual relative dimensions.

The present application discloses systems and methods for performing predictive weighting of hypotension profiling parameters. By converting data received from a hemodynamic sensor to digital hemodynamic data of a living subject, and by transforming the digital hemodynamic data to multiple hypotension profiling parameters, the present solution employs a powerful multivariate model for predicting future hypotension.

The solution disclosed by the present application utilizes the multivariate model to determine a risk score corresponding to the probability of a future hypotension event for the living subject based on a weighed combination of the multiple hypotension profiling parameters. In addition, by invoking a sensory alarm if the risk score satisfies a predetermined risk criterion, the present application discloses a solution that provides an early warning of a future hypotension event for the living subject, thereby advantageously enabling health care workers to prepare a timely and effective intervention.

FIG. 1 shows a diagram of an exemplary system for performing predictive weighting of hypotension profiling parameters, according to one implementation. Health monitoring system 100 includes hardware unit 102, which may be an integrated hardware unit, for example, including system processor 104, implemented as a hardware processor, analog-to-digital converter (ADC) 122, and system memory 106. As shown in FIG. 1, health monitoring system 100 also includes hypotension prediction software code 110 including predictive weighting module 116, stored in system memory 106. System memory 106 is further shown to store hypotension profiling parameters 112 including one or more vital sign parameters characterizing vital sign data, which will be described in greater detail below.

As further shown in FIG. 1, health monitoring system 100 also includes hemodynamic sensor 140 coupled to hardware unit 102, and display 126 providing user interface 120. In addition, health monitoring system 100 includes digital-to-analog converter 124 (hereinafter "DAC 124"), digital hemodynamic data 144 generated by ADC 122 from signal 142 received from hemodynamic sensor 140, and sensory alarm 128.

Health monitoring system 100 may be implemented within a patient care environment such as an intensive care unit (ICU) or operating room (OR), for example. As shown in FIG. 1, in addition to health monitoring system 100, the patient care environment includes patient 130 (hereinafter "living subject 130"), and healthcare worker 150 (hereinafter "user 150") trained to utilize health monitoring system 100. As will be discussed in greater detail below, user interface 120 is configured to receive inputs 152 from user 150, and to provide sensory alarm 128 if a risk score predictive of a future hypotension event for living subject 130 satisfies a predetermined risk criterion.

Hemodynamic sensor 140 is shown in an exemplary implementation in FIG. 1, and is attached to living subject 130. It is noted that hemodynamic sensor 140 may be a non-invasive or minimally invasive sensor attached to living subject 130. In one implementation, as represented in FIG. 1, hemodynamic sensor 140 may be attached non-invasively at an extremity of living subject 130, such as a wrist or finger of living subject 130. Although not explicitly shown in FIG. 1, in other implementations, hemodynamic sensor 140 may be attached non-invasively at an ankle or toe of living subject 130. Signal 142 received by health monitoring system 100 from hemodynamic sensor 140 may include signals corresponding to the arterial pressure of living subject 130, such as an arterial pressure waveform of living subject 130. Health monitoring system 100 and hemodynamic sensor 140 may be configured such that signal 142 may be received by health monitoring system 100 wirelessly, or via a wired connection with hemodynamic sensor 140.

According to the exemplary implementation shown in FIG. 1, system processor 104 is configured to utilize ADC 122 to convert signal 142 to digital hemodynamic data 144. System processor 104 is further configured to execute hypotension prediction software code 110 to transform digital hemodynamic data 144 to multiple hypotension profiling parameters 112. It is noted that hypotension profiling parameters 112 include one or more vital sign parameters characterizing vital sign data, as well as differential and combinatorial parameters derived from the one or more vital sign parameters.

System processor 104 is further configured to execute hypotension prediction software code 110 to use predictive weighting module 116 to determine a risk score corresponding to the probability of a future hypotension event for living subject 130 based on a weighted combination of hypotension profiling parameters 112. In addition, system processor 104 is configured to execute hypotension prediction software code 110 to invoke sensory alarm 128 if the risk score satisfies a predetermined risk criterion. For example, hypotension prediction software code 110 may invoke sensory alarm 128 to warn of a hypotension event for living subject 130 predicted to occur approximately one to five minutes in the future, or up to approximately thirty minutes in the future.

In various implementations, sensory alarm 128 may be implemented as one or more of a visual alarm, an audible alarm, and a haptic alarm. For example, when implemented to provide a visual alarm, sensory alarm 128 may be invoked as flashing and/or colored graphics shown by user interface 120 on display 126, and/or may include displaying the risk score via user interface 120 on display 126. When implemented to provide an audible alarm, sensory alarm 128 may be invoked as any suitable warning sound, such as a siren or repeated tone. Moreover, when implemented to provide a haptic alarm, sensory alarm 128 may cause hardware unit 102 to vibrate or otherwise deliver a physical impulse perceptible to user 150.

It is noted that the risk score of living subject 130 is determined based on a weighted combination of hypotension profiling parameters 112, which are derived from signal 142 of living subject 130 received from hemodynamic sensor 140. Consequently, according to the inventive concepts disclosed by the present application, system processor 104 of health monitoring system 100 is configured to execute hypotension prediction software code 110 to determine the risk score of living subject 130 without comparison with data corresponding to hypotension in other living subjects. In other words, hypotension prediction software code 110 determines the risk score of living subject 130 based on quantities derived from the one or more vital sign parameters characterizing vital sign data, without reference to a hypotension patient database storing information regarding hypotension in patients other than living subject 130.

In addition to the functionality described above, in some implementations, system processor 104 may be configured to execute hypotension prediction software code 110 to identify a most probable cause of the future hypotension event for living subject 130. For example, based on indicia included in digital hemodynamic data 144, hypotension prediction software code 110 may be able to identify poor vascular tone, low blood volume, or reduced cardiac contractility, to name a few exemplary causes, as a most probable cause of a predicted future hypotension event. Furthermore, in some implementations, system processor 104 may be configured to execute hypotension prediction software code 110 to recommend a medical intervention for preventing the future hypotension event for living subject 130. With respect to the first and second example causes of hypotension identified above, administration of a vasoconstrictor may be recommended if poor vascular tone is detected, while administration of saline or whole blood may be recommend if low blood volume is identified as a most probable cause of the predicted future hypotension event.

Figure 2A:
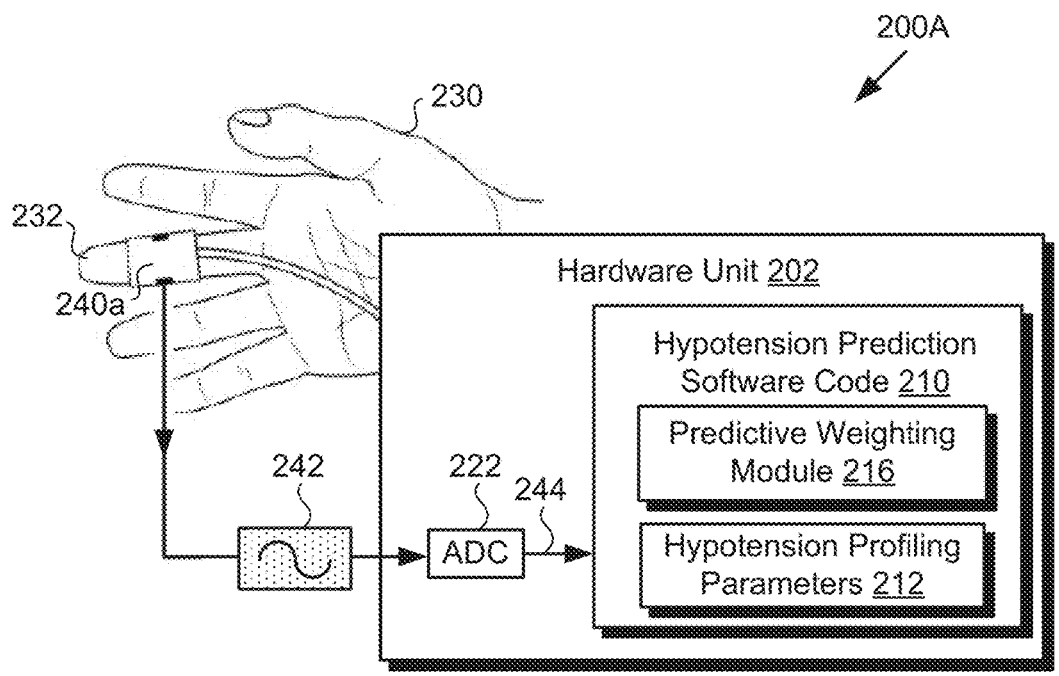
FIG. 2A shows an exemplary implementation for non-invasively detecting arterial pressure at an extremity of a living subject.

Referring to FIG. 2A, FIG. 2A shows an exemplary implementation for sensing arterial pressure non-invasively at an extremity of a living subject. Health monitoring system 200A, in FIG. 2A, includes hardware unit 202 having ADC 222 and hypotension prediction software code 210 including predictive weighting module 216. As shown by FIG. 2A, the arterial pressure of living subject 230 is detected non-invasively at finger 232 of living subject 230 using hemodynamic sensing cuff 240a. Also shown in FIG. 2A are signal 242 received by health monitoring system 200A from hemodynamic sensing cuff 240a, digital hemodynamic data 244 generated by ADC 222 from signal 242, and hypotension profiling parameters 212 including one or more vital sign parameters characterizing vital sign data, obtained through transformation of digital hemodynamic data 244 by hypotension prediction software code 210.

Living subject 230, signal 242, and hemodynamic sensing cuff 240a correspond respectively in general to living subject 130, signal 142, and hemodynamic sensor 140, in FIG. 1, and may share any of the characteristics attributed to those corresponding features in the present application. Moreover, hardware unit 202 having ADC 222 and hypotension prediction software code 210 including predictive weighting module 216, in FIG. 2A, corresponds in general to hardware unit 102 having ADC 122 and hypotension prediction software code 110 including predictive weighting module 116, in FIG. 1, and may share any of the characteristics attributed to that corresponding feature in the present application.

According to the implementation shown in FIG. 2A, hemodynamic sensing cuff 240a is designed to sense an arterial pressure of living subject 230 non-invasively at finger 232 of living subject 230. Moreover, as shown in FIG. 2A, hemodynamic sensing cuff 240a may take the form of a small, lightweight, and comfortable hemodynamic sensor suitable for extended wear by living subject 230. It is noted that although hemodynamic sensing cuff 240a is shown as a finger cuff, in FIG. 2A, in other implementations, hemodynamic sensing cuff 240a may be suitably adapted as a wrist, ankle, or toe cuff for attachment to living subject 230.

It is further noted that the advantageous extended wear capability described above for hemodynamic sensing cuff 240a when implemented as a finger cuff may also be attributed to wrist, ankle, and toe cuff implementations. As a result, hemodynamic sensing cuff 240a may be configured to provide substantially continuous beat-to-beat monitoring of the arterial pressure of living subject 230 over an extended period of time, such as minutes or hours, for example.

Figure 2B:
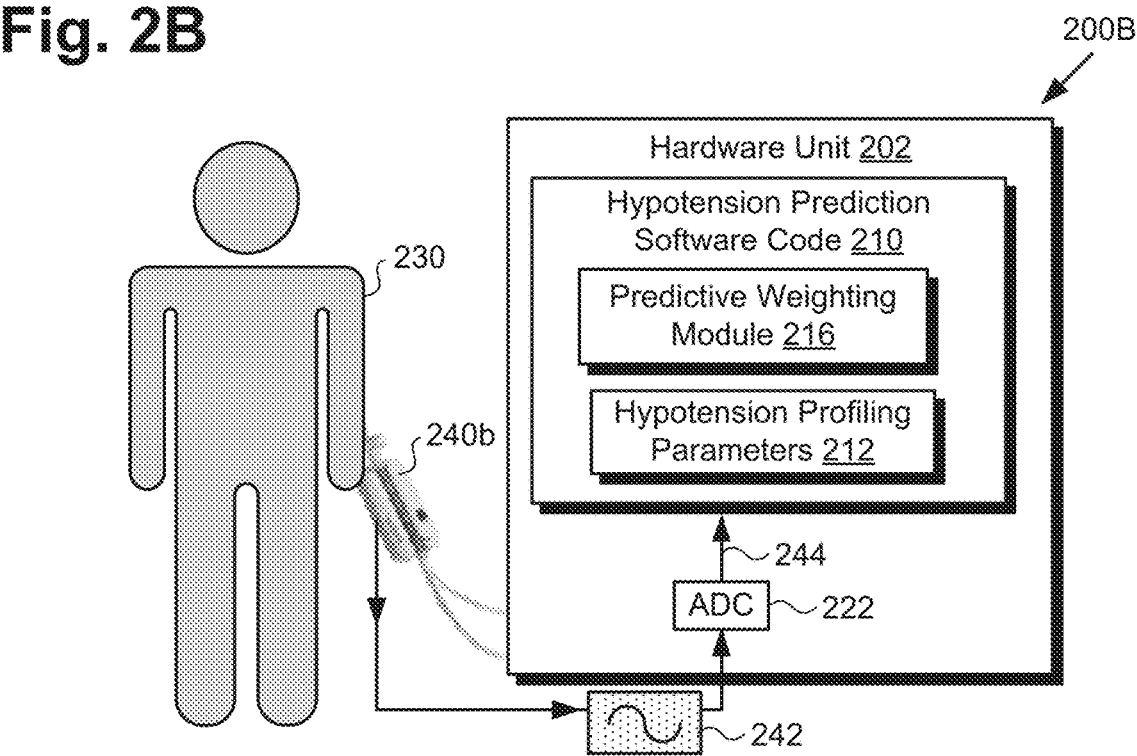
FIG. 2B shows an exemplary implementation for performing minimally invasive detection of arterial pressure of a living subject.

Continuing to FIG. 2B, FIG. 2B shows an exemplary implementation for performing minimally invasive detection of arterial pressure of a living subject. As shown by FIG. 2B, the arterial pressure of living subject 230 is detected via minimally invasive hemodynamic sensor 240b. It is noted that the features shown in FIG. 2B and identified by reference numbers identical to those shown in FIG. 2A correspond respectively to those previously described features, and may share any of the characteristics attributed to them above. It is further noted that hemodynamic sensor 240b corresponds in general to hemodynamic sensor 140, in FIG. 1, and may share any of the characteristics attributed to that corresponding feature in the present application.

According to the implementation shown in FIG. 2B, hemodynamic sensor 240b is designed to sense an arterial pressure of living subject 230 in a minimally invasive manner. For example, hemodynamic sensor 240b may be attached to living subject 230 via a radial arterial catheter inserted into an arm of living subject 230. Alternatively, and although not explicitly represented in FIG. 2B, in another implementation, hemodynamic sensor 240b may be attached to living subject 230 via a femoral arterial catheter inserted into a leg of living subject 230. Like non-invasive hemodynamic sensing cuff 240a, in FIG. 2A, minimally invasive hemodynamic sensor 240b, in FIG. 2B, may be configured to provide substantially continuous beat-to-beat monitoring of the arterial pressure of living subject 230 over an extended period of time, such as minutes or hours, for example.

Figure 3:
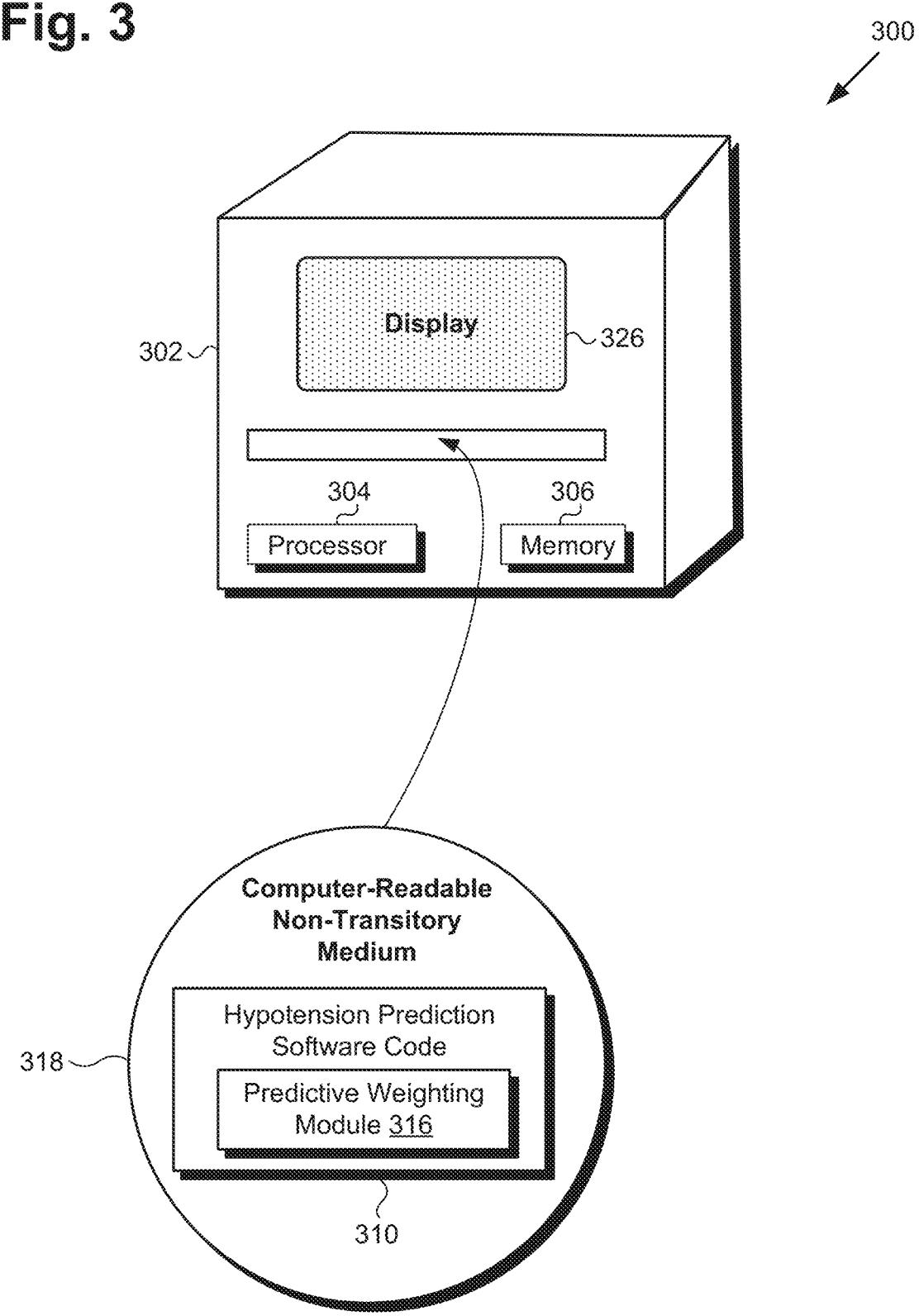
FIG. 3 shows an exemplary system and a computer-readable non-transitory medium including instructions enabling performance of predictive weighting of hypotension profiling parameters.

Moving now to FIG. 3, FIG. 3 shows an exemplary system and a computer-readable non-transitory medium including instructions enabling performance of predictive weighting of hypotension profiling parameters. System 300, in FIG. 3, includes hardware unit 302 including system processor 304, system memory 306, and display 326. Display 326 may take the form of a liquid crystal display (LCD), a light-emitting diode (LED) display, an organic light-emitting diode (OLED) display, or another suitable display screen that performs a physical transformation of signals to light. System 300 including hardware unit 302 having system processor 304 and system memory 306 corresponds in general to health monitoring system 100 including hardware unit 102 having system processor 104 and system memory 106, and may share any of the characteristics attributed to that corresponding feature in the present application. That is to say, system 302 may be configured to provide user interface 120 and/or sensory alarm 128 using display 326.

Also shown in FIG. 3 is computer-readable non-transitory medium 318 having hypotension prediction software code 310 including predictive weighting module 316 stored thereon. The expression "computer-readable non-transitory medium," as used in the present application, refers to any medium, excluding a carrier wave or other transitory signal, that provides instructions to system processor 304 of hardware unit 302. Thus, a computer-readable non-transitory medium may correspond to various types of media, such as volatile media and non-volatile media, for example. Volatile media may include dynamic memory, such as dynamic random access memory (dynamic RAM), while non-volatile memory may include optical, magnetic, or electrostatic storage devices. Common forms of computer-readable non-transitory media include, for example, optical discs, RAM, programmable read-only memory (PROM), erasable PROM (EPROM), and FLASH memory.

According to the implementation shown in FIG. 3, computer-readable non-transitory medium 318 provides hypotension prediction software code 310 including predictive weighting module 316 for execution by system processor 304. Hypotension prediction software code 310, when executed by system processor 304, instantiates a hypotension prediction software code corresponding to hypotension prediction software code 110/210 including predictive weighting module 116/216, in FIG. 1/2, and capable of performing all of the operations performed by that corresponding feature and described in the present application.

Figure 4:
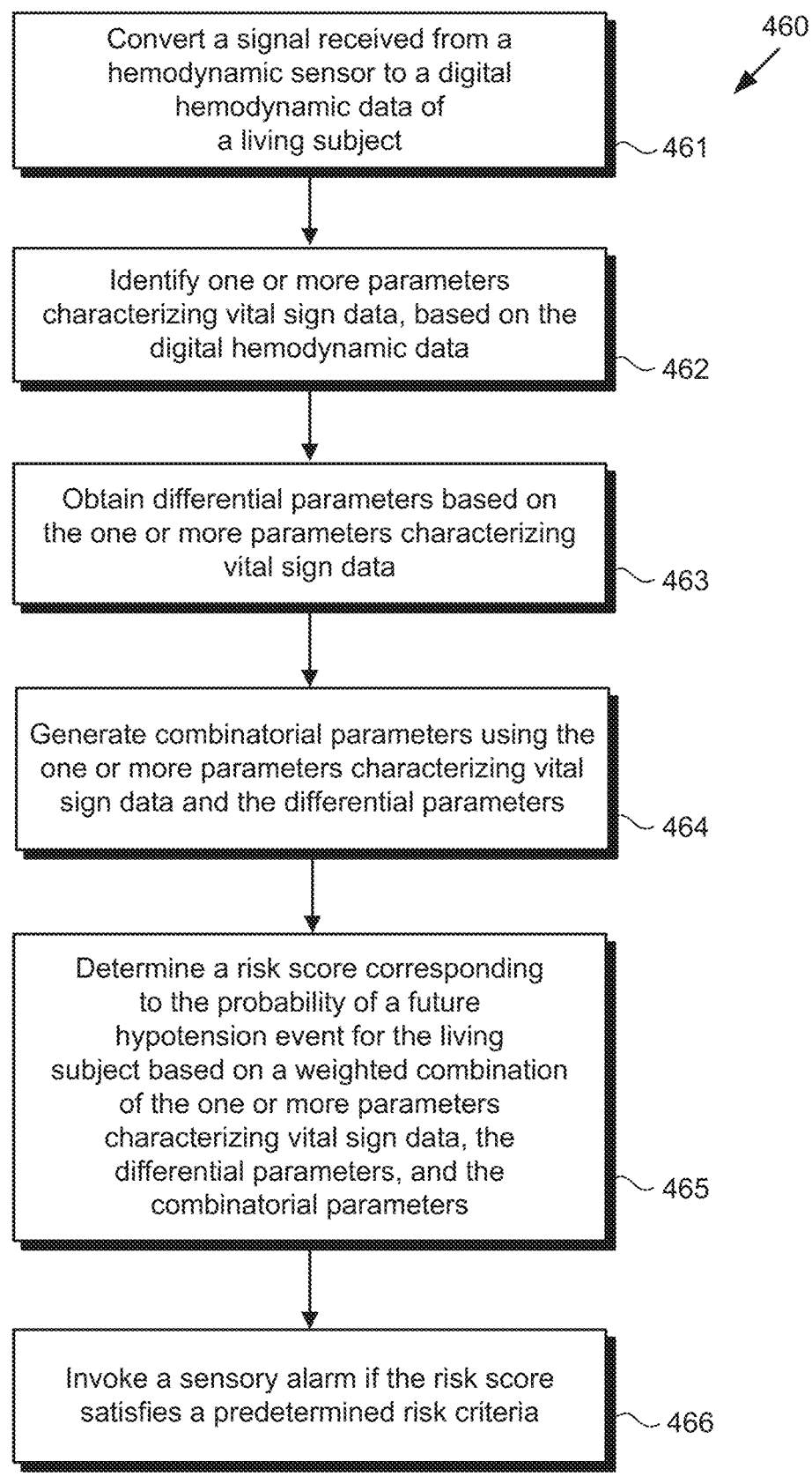
FIG. 4 is a flowchart presenting an exemplary method for use by a health monitoring system to perform predictive weighting of hypotension profiling parameters.
Figure 5:
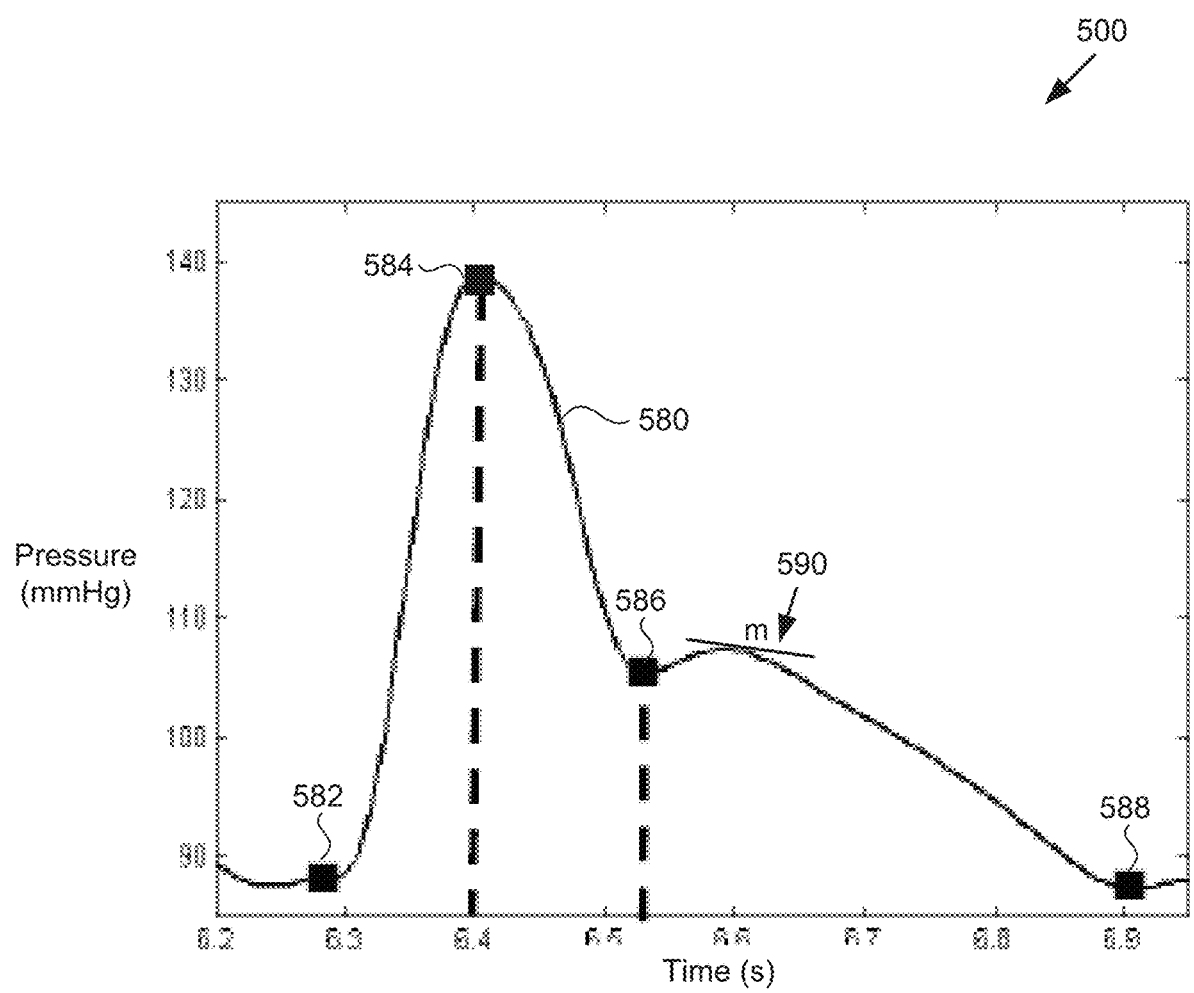
FIG. 5 shows a trace of an arterial pressure waveform including exemplary indicia corresponding to the probability of future hypotension in a living subject.

Example implementations of the present inventive concepts will be further described below with reference to FIG. 4 and FIG. 5. FIG. 4 presents flowchart 460 outlining an exemplary method for use by a health monitoring system to perform predictive weighting of hypotension profiling parameters, while FIG. 5 shows a trace of an arterial pressure waveform including exemplary indicia corresponding to the probability of future hypotension in a living subject. The method outlined in flowchart 460 can be performed using hypotension prediction software code 110/210/310 including predictive weighting module 116/216/316 described above.

Flowchart 460 begins with obtaining by hypotension prediction software code 110/210/310 executed by system processor 104/304, digital hemodynamic data 144/244 converted, by ADC 122/222, from signal 142/242 received from hemodynamic sensor 140/240a/240b (action 461). In one implementation, for example, hemodynamic sensor 140/240a/240b may be used to sense an arterial pressure of living subject 130/230 at an extremity of living subject 130/230, and to determine a central arterial pressure of living subject 130/230 based on the sensed arterial pressure.

Hardware unit 102/202/302 of system 100/200A/200B/300 may be configured to receive the determined central arterial pressure of living subject 130/230 as signal 142/242, which may be received as analog signals. In such an implementation, ADC 122/222 is used to convert signal 142/242 into digital hemodynamic data 144/244. It is noted that in other implementations, hardware unit 102/202/302 can be configured to determine the central arterial pressure of living subject 130/230 based on a peripheral or brachial arterial pressure, for example, sensed by hemodynamic sensor 140/240a/240b and received by hardware unit 102/202/302 as signal 142/242.

Referring to diagram 500, in FIG. 5, digital hemodynamic data 144/244 may include various indicia predictive of a future hypotension event for living subject 130/230 and extracted from arterial pressure waveform 580, which may be a central arterial pressure waveform of living subject 130/230. Diagram 500 shows exemplary indicia 582, 584, 586, and 588, corresponding respectively to the start of a heartbeat, the maximum systolic pressure marking the end of systolic rise, the presence of the dicrotic notch marking the end of systolic decay, and the diastole of the heartbeat of living subject 130/230. Also shown by diagram 500 is exemplary slope 590 of arterial pressure waveform 580. It is noted that slope 590 is merely representative of multiple slopes that may be measured at multiple locations along arterial pressure waveform 580.

In addition to the indicia 582, 584, 586, and 588 of arterial pressure waveform 580 per se, the behavior of arterial pressure waveform 580 during the intervals between those indicia may also be used as indicia predictive of future hypotension for living subject 130/240. For example, the interval between the start of the heartbeat at indicia 582 and the maximum systolic pressure at indicia 584 marks the duration of the systolic rise (hereinafter "systolic rise 582-584"). The systolic decay of arterial pressure waveform 580 is marked by the interval between the maximum systolic pressure at indicia 584 and the dicrotic notch at indicia 586 (hereinafter "systolic decay 584-586"). Together, systolic rise 582-584 and systolic decay 584-586 mark the entire systolic phase (hereinafter "systolic phase 582-586"), while the interval between the dicrotic notch at indicia 586 and the diastole at indicia 588 mark the diastolic phase of arterial pressure waveform 580 (hereinafter "diastolic phase 586-588").

Also of potential diagnostic interest is the behavior of arterial pressure waveform 580 in the interval from the maximum systolic pressure at indicia 584 to the diastole at indicia 588 (hereinafter "interval 584-588"), as well as the behavior of arterial pressure waveform 580 from the start of the heartbeat at indicia 582 to the diastole at indicia 588 (hereinafter "heartbeat interval 582-588"). The behavior of arterial pressure waveform 580 during intervals: 1) systolic rise 582-584, 2) systolic decay 584-586, 3) systolic phase 582-586, 4) diastolic phase 586-588, 5) interval 584-588, and 6) heartbeat interval 582-588 may be determined by measuring the area under the curve of arterial pressure waveform 580 and the standard deviation of arterial pressure waveform 580 in each of those intervals, for example. The respective areas and standard deviations measured for intervals 1, 2, 3, 4, 5, and 6 above (hereinafter "intervals 1-6") may serve as additional indicia predictive of future hypotension for living subject 130/240.

Flowchart 460 continues with obtaining, by hypotension prediction software code 110/210/310 executed by system processor 104/304, one or more vital sign parameters characterizing vital sign data, i.e., characterizing vital sign data of living subject 130/230, from digital hemodynamic data 144/244 (action 462). As noted above, digital hemodynamic data 144/244 may include any or all of indicia 582, 584, 586, 588, and 590. In addition, digital hemodynamic data 144/244 may further include the respective areas and standard deviations measured for intervals 1-6 of arterial pressure waveform 580, as discussed above. According to the exemplary implementations shown in FIGS. 1, 2A, and 2B, digital hemodynamic data 144/244 is received by hypotension prediction software code 110/210/310 from ADC 122/222.

The one or more vital sign parameters characterizing vital sign data may include stroke volume, heart rate, respiration, and cardiac contractility, to cite a few examples. Moreover, the one or more vital sign parameters characterizing vital sign data may include a variety of different types of parameters found to be predictive of future hypotension. For instance, the one or more vital sign parameters characterizing vital sign data may include any or all of mean arterial pressure (MAP), baroreflex sensitivity measures, hemodynamic complexity measures, and frequency domain hemodynamic features.

Baroreflex sensitivity measures quantify the relationship between complementary physiological processes. For example, a decrease in blood pressure in a healthy living subject is typically compensated by an increase in heart rate and/or an increase in peripheral resistance. The baroreflex sensitivity measures that may be included in the one or more vital sign parameters characterizing vital sign data correspond to the degree to which living subject 130/230 is responding appropriately to normal physiological variations.

Hemodynamic complexity measures quantify the amount of regularity in cardiac measurements over time, as well as the entropy, i.e., the unpredictability of fluctuations in cardiac measurements over time. For example, the present inventors have realized that unpredictable cardiac fluctuations are a normal phenomenon associated with health. Perhaps counterintuitively, very low entropy, in other words a high degree of regularity in cardiac measurements over time and the substantial absence of unpredictable fluctuations, can be a significant warning sign of an impending hypotension event. Frequency domain hemodynamic features quantify various measures of cardiac performance as a function of frequency rather than time.

Flowchart 460 continues with deriving differential parameters based on the one or more vital sign parameters characterizing vital sign data (action 463). Obtaining differential parameters based on the one or more vital sign parameters (hereinafter "the differential parameters") may be performed by hypotension prediction software code 110/210/310 executed by system processor 104/304. The differential parameters may be derived by determining the variations of one or more vital sign parameters with respect to time, with respect to frequency, or with respect to other parameters from among one or more vital sign parameters, for example. As a result, each of one or more vital sign parameters may give rise to one, two, or several differential parameters included among hypotension profiling parameters 112/212.

For example, the differential parameter stroke volume variation (SVV) may be derived based on changes in the parameter stroke volume (SV) as a function of time and/or as a function of sampling frequency. Analogously, changes in mean arterial pressure (ΔMAP) can be derived as a differential parameter with respect to time and/or sampling frequency, and so forth. As a further example, changes in mean arterial pressure with respect to time can be derived by subtracting the average of the mean arterial pressure over the past 5 minutes, over the past 10 minutes, and so on from the current value of the mean arterial pressure.

Flowchart 460 continues with generating combinatorial parameters using the one or more vital sign parameters and the differential parameters (action 464). Generation of such combinatorial parameters (hereinafter "the combinatorial parameters") may be performed by hypotension prediction software code 110/210/310 executed by system processor 104/304. For example, the combinatorial parameters may be generated using the one or more vital sign parameters and the differential parameters by generating a power combination of a subset of the one or more vital sign parameters and the differential parameters. It is noted that, as used in the present application, the characterization "a subset of the one or more vital sign parameters and the differential parameters" refers to a subset that includes at least one of the one or more vital sign parameters and/or at least one of the differential parameters.

As a specific example, each of the combinatorial parameters may be generated as a power combination of three parameters, which may be randomly or purposefully selected, from among the one or more vital sign parameters characterizing vital sign data and/or the differential parameters. Each of those three parameters selected from among the one or more vital sign parameters and/or the differential parameters can be raised to an exponential power and can be multiplied with, or added to, the other two parameters analogously raised to an exponential power. The exponential power to which each of the three parameters selected from the one or more vital sign parameters and/or the differential parameters is raised may be, but need not be, the same.

In some implementations, for example, generation of the combinatorial parameters may be performed using a predetermined and limited integer range of exponential powers. For instance, in one such implementation, the exponential powers used to generate the combinatorial parameters may be integer powers selected from among negative two, negative one, zero, one, and two (−2, −1, 0, 1, 2). Thus, each combinatorial parameter may take the form:

$$X = Y_1^a * Y_2^b * \ldots Y_n^e \quad \text{(Equation 1)}$$

where each Y is one of one or more vital sign parameters characterizing vital sign data or one of the differential parameters, n is any integer greater than two, and each of a, b, and c may be any one of −2, −1, 0, 1, and 2, for example. In one implementation, Equation 1 may be applied to substantially all possible power combinations of the one or more vital sign parameters, the differential parameters, and the one or more vital sign parameters with the differential parameters, subject to the predetermined constraints discussed above, such as the value of n and the numerical range from which the exponential powers may be selected.

Hypotension profiling parameters 112/212 include one or more vital sign parameters characterizing vital sign data, the differential parameters and the combinatorial parameters. Thus, actions 462, 463, and 464 result in transformation of digital hemodynamic data 144/244 to hypotension profiling parameters 112/212. That is to say, digital hemodynamic data 144/244 is transformed to hypotension profiling parameters 112/212 using hypotension prediction software code 110/210/310, executed by system processor 104/304, by identifying one or more vital sign parameters characterizing vital sign data, based on digital hemodynamic data 144/244, obtaining the differential parameters based on one or more vital sign parameters, and generating the combinatorial parameters using one or more of vital sign parameters and the differential parameters. An exemplary but non-exhaustive table of hypotension profiling parameters 112/212, as well as exemplary sampling criteria associated with their determination, is provided as Appendix A of the present application.

Flowchart 460 continues with determining, by hypotension prediction software code 110/210/310 using predictive weighting module 116/216/316 and executed by system processor 104/304, a risk score corresponding to the probability of a future hypotension event for living subject 130/230 based on a weighted combination of hypotension profiling parameters 112/212 (action 465). In other words, the risk score corresponding to the probability of a future hypotension event for living subject 130/230 is determined based on the one or more vital sign parameters characterizing vital sign data, the differential parameters and the combinatorial parameters.

It is noted that in implementations in which one or more vital sign parameters characterizing vital sign data includes the MAP of living subject 130/230, the weighting applied to the MAP may depend on the value of the MAP itself. Where the MAP is very high, the MAP may be a relatively unreliable predictor of hypotension and may consequently be very lightly weighted. That is to say, where the MAP exceeds a predetermined upper limit threshold, for example, the weighting applied to the MAP may be such that the weighted combination of hypotension profiling parameters 112/212 results in the MAP being substantially disregarded in determination of the risk score. By contrast, in other cases, the MAP may dominate the determination of the risk score.

It is emphasized that the risk score of living subject 130/230 is determined based on a weighted combination of hypotension profiling parameters 112/212, which in turn are derived from signal 142/242 of living subject 130/230 received from hemodynamic sensor 140/240a/240b. Consequently, according to the inventive concepts disclosed by the present application, system processor 104/304 of health monitoring system 100/200A/200B/300 is configured to execute hypotension prediction software code 110/210/310 to determine the risk score of living subject 130/230 without comparison with data corresponding to hypotension in other living subjects. In other words, hypotension prediction software code 110/210/310 determines the risk score of living subject 130/230 based on quantities derived from digital hemodynamic data 144/244, i.e., hypotension profiling parameters 112/212, without reference to a hypotension patient database storing information regarding hypotension in patients other than living subject 130/230.

By way merely of example, the risk score may be expressed as:

$$\text{Risk Score} = 1/(1+e^{-A}) \quad \text{(Equation 2)}$$

Where:

$$A = c_0 + c_1 \times v_1 + c_2 \times v_2 + c_3 \times v_3 + c_4 \times v_4 + c_5 \times v_5 + c_6 \times v_6 +$$
$$c_7 \times v_7^2 \times v_8^2 \times v_9^{-2} + c_8 \times v_2^2 \times v_{10} \times v_{11}^{-1} + c_9 \times \Delta(v_{12}^2 \times v_{13}^2 \times v_{14}) +$$

-continued $$c_{10} \times \Delta(v_{15}^2 \times v_1 \times v_{16}^{-1}) + c_{11} \times \Delta(v_{17}^2 \times v_{18}^2 \times v_{19}^{-2})$$

And where:
e=Euler's number, a constant about equal to 2.71828
$v_1$=CWI, the cardiac work indexed by patient's body surface area;
$v_2$=MAPavg, the averaged mean arterial pressure;
$v_3$=ΔMAPavg, the change of averaged mean arterial pressure when compared to initial values;
$v_4$=avgSysDec, the averaged pressure at the decay portion of the systolic phase;
$v_5$=ΔSys, the change of systolic pressure when compared to initial values;
$v_6$=ppAreaNor, the normalized area under the arterial pressure waveform;
$v_7$=biasDia, the bias of the diastolic slope;
$v_8$=CW, the cardiac work;
$v_9$=mapDnlocArea, the area under the arterial pressure waveform, between first instance of MAP and the dicrotic notch;
$v_{10}$=SWcomb, the stroke work;
$v_{11}$=ppArea, the area under the arterial pressure waveform;
$v_{12}$=decAreaNor, the normalized area of the decay phase;
$v_{13}$=slopeSys, the slope of the systolic phase;
$v_{14}$=Cwk, the Windkessel compliance;
$v_{15}$=sys_rise_area_nor, the normalized area under the systolic rise phase;
$v_{16}$=pulsepres, the pulse pressure;
$v_{17}$=avg_sys, the averaged pressure of the systolic phase;
$v_{18}$=dpdt2, the maximum value of the second order derivative of the pressure waveform;
$v_{19}$=dpdt, the maximum value of the first order derivative of the pressure waveform; and
Δ=the change of the value when compared to its initial value $c_0, c_1, \ldots, c_{11}$ are constant coefficients.

In some implementations, the risk score may be expressed as a fraction, as represented by Equation 2. However, in other implementations, the risk score may be converted to a percentage risk score between zero percent and one hundred percent.

Flowchart 460 can conclude with invoking, by hypotension prediction software code 110/210/310 executed by system processor 104/304, sensory alarm 128 if the risk score satisfies a predetermined risk criterion (action 466). As shown in FIG. 1, for example, hypotension prediction software code 110/210/310 may be configured to provide an output to user interface 120 on display 126/326 for displaying the risk score, and/or for invoking sensory alarm 128. As further shown in FIG. 1, in some implementations, the output of hypotension prediction software code 110/210/310 may be processed using DAC 124 to convert digital signals into analog signals for presentation via user interface 120.

The predetermined risk criterion may be based on the value of the risk score, on the trend of the risk score over a time interval, or both. For example, where the risk score is expressed as a percentage between zero and one hundred, having the risk score exceed a threshold of eighty-five percent, for instance, may cause sensory alarm 128 to be invoked immediately. Alternatively, or in addition, a lower risk score may cause sensory alarm 128 to be invoked if it exceeds a predetermined threshold over the entirety of a predetermined time period.

Thus, for example, while a risk score of eighty five percent may cause sensory alarm 128 to be invoked immediately, a risk score of eighty percent may cause sensory alarm 128 to be invoked after several seconds at that level, such as ten to thirty seconds in which the risk score is continuously between eighty and eighty five percent, for example. By analogy, a still lower risk score may cause sensory alarm 128 to be invoked if that risk score is maintained continuously for one or more minutes. In yet another implementation, the risk score may cause sensory alarm 128 to be invoked if it meets or exceeds a predetermined value a predetermined number of times over a predetermined time period. For example, having the risk score exceed seventy five percent three times over a five minute interval may cause sensory alarm 128 to be invoked.

As noted above by reference to FIG. 1, sensory alarm 128 may be implemented as one or more of a visual alarm, an audible alarm, and a haptic alarm. For example, when implemented to provide a visual alarm, sensory alarm 128 may be invoked as flashing and/or colored graphics shown by user interface 120 on display 126, and/or may include displaying the risk score via user interface 120 on display 126/326. When implemented to provide an audible alarm, sensory alarm 128 may be invoked as any suitable warning sound, such as a siren or repeated tone. Moreover, when implemented to provide a haptic alarm, sensory alarm 128 may cause hardware unit 102/302 to vibrate or otherwise deliver a physical impulse perceptible to user 150.

Although not included among the actions outlined by flowchart 460, in some implementations, the present method may include identifying, by hypotension prediction software code 110/210/310 executed by system processor 104/304, a most probable cause of the future hypotension event of living subject 130/230. For example, and as noted above, based on indicia included in digital hemodynamic data 144/244, hypotension prediction software code 110/210/310 may be used to identify poor vascular tone, low blood volume, or reduced cardiac contractility, to name a few exemplary causes, as a most probable cause of a predicted future hypotension event.

In addition, in some implementations, the present method may include recommending, by hypotension prediction software code 110/210/310 executed by system processor 104/304, a medical intervention for preventing the future hypotension event of living subject 130/230. With respect to poor vascular tone or low blood volume, for example, administration of a vasoconstrictor may be recommended if poor vascular tone is detected, while administration of saline or whole blood may be recommend if low blood volume is identified as a most probable cause of the predicted future hypotension event.

Thus, by converting data received from a hemodynamic sensor to digital hemodynamic data of a living subject, and by transforming the digital hemodynamic data to multiple hypotension profiling parameters, the present solution employs a powerful multivariate model for predicting future hypotension. The solution disclosed by the present application then determines a risk score corresponding to the probability of a future hypotension event for the living subject based on a weighed combination of the multiple hypotension profiling parameters. In addition, by invoking a sensory alarm if the risk score satisfies a predetermined risk criterion, the present application discloses a solution that provides an early warning of a future hypotension event for the living subject, thereby advantageously enabling health care workers to prepare a timely and effective intervention.

From the above description it is manifest that various techniques can be used for implementing the concepts described in the present application without departing from the scope of those concepts. Moreover, while the concepts have been described with specific reference to certain implementations, a person of ordinary skill in the art would recognize that changes can be made in form and detail without departing from the scope of those concepts. As such, the described implementations are to be considered in all respects as illustrative and not restrictive. It should also be understood that the present application is not limited to the particular implementations described herein, but many rearrangements, modifications, and substitutions are possible without departing from the scope of the present disclosure.

APPENDIX A

| Hypotension Profiling Parameter Description | Sampling Criteria |
|---|---|
| 1. TR_bp_dia: Diastolic pressure | 20 sec. average |
| 2. TR_c_wk: The Windkessel Compliance (based on the Langewooters paper) | 20 sec. average |
| 3. TR_CO_disp: Cardiac output | 20 sec. average |
| 4. TR_CO_hsi: Cardiac output computed with a heavily weighted multivariate model based on hyperdynamic conditions | 20 sec. average |
| 5. TR_COaccum_avg: Cardiac output - 5 min. average | 5 min. average |
| 6. TR_dia_area_nodia: Area under the arterial pressure waveform from the dicrotic notch to the start of the next beat with subtracted diastolic pressure | 20 sec. average |
| 7. TR_dpdt_var: Variability in maximum of the first derivative | 20 sec. average |
| 8. TR_dpdt2_var: Variability in maximum of the second derivative | 20 sec. average |
| 9. TR_HR_avg_disp: Heart rate - 5 min. average | 5 min. average |
| 10. TR_K_avg_fp_tp: Multivariate classification model to detect the likelihood of a false positive in the prediction of K_avg_dm | 20 sec. average |
| 11. TR_t_sys_rise_var: Variability in TR_t_sys_rise | 20 sec. average |
| 12. TR_K_avg_hyp_w: Vascular tone computed from a weighted multivariate model derived from severe hyperdynamic conditions | 20 sec. average |
| 13. TR_K_avg_lco: Multivariate classification model to detect low flow conditions | 20 sec. average |
| 14. TR_kmult: Arterial tone estimate | 20 sec. average |
| 15. TR_kmult_fp_tp: K_avg_fp_tp - 20 sec. Average | 20 sec. average |
| 16. TR_kurt: The kurtosis of the arterial pressure waveform within a beat | 20 sec. average |
| 17. TR_kurt_var: Variability in the kurtosis of the arterial pressure waveform within a beat | 20 sec. average |
| 18. TR_sku: Skewness of the arterial pressure waveform within a beat | 20 sec. average |
| 19. TR_sku_var: Variability in TR_sku | 20 sec. average |
| 20. TR_sku2: Skewness of the 20 sec. reconstructed arterial pressure waveform | 20 sec. average |
| 21. TR_slope_dia: Diastolic slope | 20 sec. average |
| 22. TR_slope_dia_var: Variability in the diastolic slope | 20 sec. average |
| 23. TR_slope_sys: Slope of the systolic rise | 20 sec. average |
| 24. TR_SVV_avg_disp: Stroke volume variation (SVV) - 5 min. average | 5 min. average |
| 25. TR_SVV_disp: SVV sensed by hemodynamic sensor 140/240a/240b | 20 sec. average |
| 26. TR_SVV_resp: SVV computed with the detection of the respiratory cycles in the signal | 20 sec. average |
| 27. TR_t_dec_var: Variability in time from systolic maximum to start of next heart beat | 20 sec. average |
| 28. TR_t_sys: Duration of the systolic phase from the start of the heart beat to the dicrotic notch | 20 sec. average |
| 29. TR_t_sys_dec: Time from the systolic maximum to the dicrotic notch | 20 sec. average |
| 30. TR_t_sys_rise: Time from the start of the heart beat to the systolic maximum | 20 sec. average |

What is claimed is:

1. A system for monitoring of arterial pressure of a patient and providing a warning to medical personnel of a predicted future hypotensive event, the system comprising:
   a minimally invasive or non-invasive hemodynamic sensor that produces an analog hemodynamic sensor signal representative of an arterial pressure waveform of the patient;
   an analog-to-digital converter that converts the analog hemodynamic sensor signal to digital hemodynamic data;
   a system memory that stores hypotension prediction software code including a predictive weighting module;
   a user interface that includes a sensory alarm that provides a sensory signal to warn medical personnel of the predicted future hypotensive event prior to the patient entering a hypotensive state; and
   a hardware processor that is configured to execute the hypotension prediction software code to:
      perform waveform analysis of the digital hemodynamic data to obtain vital sign parameters from the digital hemodynamic data representing the arterial pressure waveform;
      derive differential parameters based on one or more of the vital sign parameters;
      generate combinatorial parameters using one or more of the vital sign parameters and/or one or more of the differential parameters;
      determine, using the predictive weighting module, a risk score representing a probability of a future hypotension event for the patient based on a weighted combination of a plurality of hypotension profiling parameters including the one or more of the vital sign parameters, the differential parameters and the combinatorial parameters; and
      invoke the sensory alarm to produce the sensory signal in response to the risk score satisfying a predetermined risk criterion;
   wherein the plurality of hypotension profiling parameters includes at least one of:
      cardiac contractility;
      kurtosis of the arterial pressure waveform within a beat; and
      variability in the kurtosis of the arterial pressure waveform within a beat.

2. The system of claim 1, wherein the hardware processor transforms the digital hemodynamic data to obtain the vital sign parameters by executing the hypotension prediction software code to:
   determine, from the digital hemodynamic data, on a heartbeat-by-heartbeat basis, indicia representative of one or more of:
      maximum systolic pressure marking end of systolic rise;
      presence of a dicrotic notch marking end of systolic decay;
      diastole of the heartbeat; and
      slopes of an arterial pressure waveform;
   determine, based on the indicia, one or more intervals from the group consisting of:
      systolic rise interval;
      systolic phase interval;
      diastolic phase interval;
      maximum systolic pressure to diastole interval; and
      heartbeat interval; and produce one or more parameters representing behavior of the arterial pressure waveform during the one or more intervals.

3. The system of claim 1, wherein the plurality of hypotension profiling parameters comprise at least one of:
stroke volume;
respiration rate;
mean arterial pressure (MAP);
baroreflex sensitivity measures;
hemodynamic complexity measures; and
frequency domain hemodynamic features.

4. The system of claim 1, wherein the hardware processor is further configured to execute the hypotension prediction software code to identify a most probable cause of the future hypotension event.

5. The system of claim 4, wherein the hardware processor is further configured to execute the hypotension prediction software code to recommend a medical intervention for preventing the future hypotension event.

6. The system of claim 1, wherein the hemodynamic sensor is a noninvasive hemodynamic sensor that is attachable to an extremity of the patient.

7. The system of claim 1, wherein the hemodynamic sensor is a minimally invasive arterial catheter based hemodynamic sensor.

8. The system of claim 1, wherein the sensory alarm comprises a visual alarm.

9. The system of claim 1, wherein the sensory alarm comprises an audible alarm.

10. The system of claim 1, wherein the sensory alarm comprises a haptic alarm.

11. The system of claim 1, wherein the vital sign parameters include one or more of stroke volume, heart rate, respiration, and cardiac contractility.

12. The system of claim 11, wherein the differential parameters are derived by the hardware processor to represent variations in one or more of the vital sign parameters with respect to time, with respect to frequency, or with respect to other vital sign parameters.

13. The system of claim 1, wherein the combinatorial parameters comprise a combination of vital sign parameters, a combination of differential parameters, or a combination of at least one vital sign parameter and at least one differential parameter.

14. The system of claim 13, wherein the combinatorial parameters comprise a multiplication or addition of vital sign parameters, a multiplication or addition of combinational parameters, or a multiplication or addition of both a vital sign parameter and a combinational parameter.

15. The system of claim 13, wherein the combinatorial parameters comprise a power combination in which each vital sign parameter and differential parameter has a corresponding exponential power.

16. The system of claim 1, wherein the hardware processor is configured to invoke the sensory alarm immediately when the risk score satisfies a first risk criterion.

17. The system of claim 16, wherein the hardware processor is configured to invoke the sensory alarm when the risk score satisfies a second risk criterion continuously for a first predetermined time period.

18. The system of claim 17, wherein the hardware processor is configured to invoke the sensory alarm when the risk score satisfies a third risk criterion continuously for a second, longer, predetermined time period.

19. The system of claim 16, wherein the hardware processor is configured to invoke the sensory alarm when the risk score satisfies a fourth risk criterion a predetermined number of times over a predetermined time interval.

20. The system of claim 1 wherein the risk score is determined by a formula:

$$\text{Risk Score} = 1/(1+e^{-A}), \text{ where:}$$

$$A = c_0 + c_1 \times v_1 + c_2 \times v_2 + c_3 \times v_3 + c_4 \times v_4 + c_5 \times v_5 + c_6 \times v_6 + c_7 \times v_7^2 \times v_8^2 \times v_9^{-2} + c_8 \times v_2^2 \times v_{10} \times v_{11}^{-1} + c_9 \times \Delta(v_{12}^2 \times v_{13}^2 \times v_{14}) + c_{10} \times \Delta(v_{15}^2 \times v_1 \times v_{16}^{-}) + c_{11} \times \Delta v_{17}^2 \times v_{18}^2 \times v_{19}^{-2}), \text{ where:}$$

$v_1$=cardiac work indexed by patient's body surface area;
$v_2$=averaged mean arterial pressure;
$v_3$=change of averaged mean arterial pressure when compared to initial values;
$v_4$=averaged pressure at a decay portion of the systolic phase;
$v_5$=change of systolic pressure when compared to initial values;
$v_6$=normalized area under an arterial pressure waveform;
$v_7$=bias of diastolic slope;
$v_8$=cardiac work;
$v_9$=area under the arterial pressure waveform, between first instance of MAP and the dicrotic notch;
$v_{10}$=stroke work;
$v_{11}$=area under the arterial pressure waveform;
$v_{12}$=normalized area of decay phase;
$v_{13}$=slope of systolic phase;
$v_{14}$=Windkessel compliance;
$v_{15}$=normalized area under systolic rise phase;
$v_{16}$=pulse pressure;
$v_{17}$=averaged pressure of systolic phase;
$v_{18}$=maximum value of a second order derivative of the arterial pressure waveform;
$v_{19}$=maximum value of a first order derivative of the arterial pressure waveform;
$\Delta$=change of a value when compared to its initial value; and
$c_0, c_1, \ldots, c_{11}$ are constant coefficients.

21. The system of claim 20, wherein the hardware processor converts the risk score to a percentage risk score between zero percent and one hundred percent.

22. A system for monitoring of arterial pressure of a patient and providing a warning to medical personnel of a predicted future hypotensive event, the system comprising:
a hemodynamic sensor that produces an analog hemodynamic sensor signal representative of an arterial pressure waveform of the patient;
an analog-to-digital converter that converts the analog hemodynamic sensor signal to digital hemodynamic data;
a system memory that stores hypotension prediction software code including a predictive weighting module;
a user interface that includes a sensory alarm that provides a sensory signal to warn medical personnel of the predicted future hypotensive event prior to the patient entering a hypotensive state; and
a hardware processor that is configured to execute the hypotension prediction software code to:
perform waveform analysis of the digital hemodynamic data to obtain vital sign parameters from the digital hemodynamic data;
derive differential parameters based on one or more of the vital sign parameters, wherein the differential parameters include stroke volume variation (SVV) based upon changes in stroke volume as a function of time or sampling frequency;

generate combinatorial parameters using one or more of the vital sign parameters and/or one or more of the differential parameters;

determine, using the predictive weighting module, a risk score representing a probability of a future hypotension event for the patient based on a weighted combination of a plurality of hypotension profiling parameters including the one or more of the vital sign parameters, the differential parameters, and the combinatorial parameters; and invoke the sensory alarm to produce the sensory signal in response to the risk score satisfying a predetermined risk criterion.

23. A system for monitoring of arterial pressure of a patient and providing a warning to medical personnel of a predicted future hypotensive event, the system comprising:

a hemodynamic sensor that produces an analog hemodynamic sensor signal representative of an arterial pressure waveform of the patient;

an analog-to-digital converter that converts the analog hemodynamic sensor signal to digital hemodynamic data;

a system memory that stores hypotension prediction software code including a predictive weighting module;

a user interface that includes a sensory alarm that provides a sensory signal to warn medical personnel of the predicted future hypotensive event prior to the patient entering a hypotensive state; and a hardware processor that is configured to execute the hypotension prediction software code to:

perform waveform analysis of the digital hemodynamic data to obtain vital sign parameters from the digital hemodynamic data;

derive differential parameters based on one or more of the vital sign parameters, wherein the differential parameters include change of mean arterial pressure ($\Delta$MAP) as a function of time or sampling frequency;

generate combinatorial parameters using one or more of the vital sign parameters and/or one or more of the differential parameters;

determine, using the predictive weighting module, a risk score representing a probability of a future hypotension event for the patient based on a weighted combination of a plurality of hypotension profiling parameters including the one or more of the vital sign parameters, the differential parameters, and the combinatorial parameters; and invoke the sensory alarm to produce the sensory signal in response to the risk score satisfying a predetermined risk criterion.

24. A system for monitoring of arterial pressure of a patient and providing a warning to medical personnel of a predicted future hypotensive event, the system comprising:

a minimally invasive or non-invasive hemodynamic sensor that produces an analog hemodynamic sensor signal representative of an arterial pressure waveform of the patient;

an analog-to-digital converter that converts the analog hemodynamic sensor signal to digital hemodynamic data;

a system memory that stores hypotension prediction software code including a predictive weighting module;

a user interface that includes a sensory alarm that provides a sensory signal to warn medical personnel of the predicted future hypotensive event prior to the patient entering a hypotensive state; and a hardware processor that is configured to execute the hypotension prediction software code to:

perform waveform analysis of the digital hemodynamic data to obtain vital sign parameters from the digital hemodynamic data representing the arterial pressure waveform;

derive differential parameters based on one or more of the vital sign parameters;

generate combinatorial parameters using one or more of the vital sign parameters and/or one or more of the differential parameters;

determine, using the predictive weighting module, a risk score representing a probability of a future hypotension event for the patient based on a weighted combination of a plurality of hypotension profiling parameters including the one or more of the vital sign parameters, the differential parameters, and the combinatorial parameters; and invoke the sensory alarm to produce the sensory signal in response to the risk score satisfying a predetermined risk criterion;

wherein the plurality of hypotension profiling parameters includes cardiac output.

25. A system for monitoring of arterial pressure of a patient and providing a warning to medical personnel of a predicted future hypotensive event, the system comprising:

a minimally invasive or non-invasive hemodynamic sensor that produces an analog hemodynamic sensor signal representative of an arterial pressure waveform of the patient;

an analog-to-digital converter that converts the analog hemodynamic sensor signal to digital hemodynamic data;

a system memory that stores hypotension prediction software code including a predictive weighting module;

a user interface that includes a sensory alarm that provides a sensory signal to warn medical personnel of the predicted future hypotensive event prior to the patient entering a hypotensive state; and a hardware processor that is configured to execute the hypotension prediction software code to:

perform waveform analysis of the digital hemodynamic data to obtain vital sign parameters from the digital hemodynamic data representing the arterial pressure waveform;

derive differential parameters based on one or more of the vital sign parameters;

generate combinatorial parameters using one or more of the vital sign parameters and/or one or more of the differential parameters;

determine, using the predictive weighting module, a risk score representing a probability of a future hypotension event for the patient based on a weighted combination of a plurality of hypotension profiling parameters including the one or more of the vital sign parameters, the differential parameters, and the combinatorial parameters; and invoke the sensory alarm to produce the sensory signal in response to the risk score satisfying a predetermined risk criterion;

wherein the plurality of hypotension profiling parameters includes at least one of arterial tone and vascular tone.

26. A system for monitoring of arterial pressure of a patient and providing a warning to medical personnel of a predicted future hypotensive event, the system comprising:

a minimally invasive or non-invasive hemodynamic sensor that produces an analog hemodynamic sensor signal representative of an arterial pressure waveform of the patient;

an analog-to-digital converter that converts the analog hemodynamic sensor signal to digital hemodynamic data;

a system memory that stores hypotension prediction software code including a predictive weighting module;

a user interface that includes a sensory alarm that provides a sensory signal to warn medical personnel of the predicted future hypotensive event prior to the patient entering a hypotensive state; and a hardware processor that is configured to execute the hypotension prediction software code to:

perform waveform analysis of the digital hemodynamic data to obtain vital sign parameters from the digital hemodynamic data representing the arterial pressure waveform;

derive differential parameters based on one or more of the vital sign parameters;

generate combinatorial parameters using one or more of the vital sign parameters and/or one or more of the differential parameters;

determine, using the predictive weighting module, a risk score representing a probability of a future hypotension event for the patient based on a weighted combination of a plurality of hypotension profiling parameters including the one or more of the vital sign parameters, the differential parameters, and the combinatorial parameters; and invoke the sensory alarm to produce the sensory signal in response to the risk score satisfying a predetermined risk criterion;

wherein the plurality of hypotension profiling parameters includes at least one of: baroreflex sensitivity measures; hemodynamic complexity measures that quantify the entropy in cardiac measurements over time; and frequency domain hemodynamic features.

* * * * *